United States Patent
Tu et al.

(10) Patent No.: US 11,421,260 B2
(45) Date of Patent: Aug. 23, 2022

(54) RAPID APPROACH FOR DETECTION OF BACTERIAL SPORES

(71) Applicant: ECOLAB USA INC., St. Paul, MN (US)

(72) Inventors: Wenli Tu, Shanhai (CN); Zhi Chen, Shanghai (CN)

(73) Assignee: ECOLAB USA INC., St. Paul, MN (US)

( * ) Notice: Subject to any disclaimer, the term of this patent is extended or adjusted under 35 U.S.C. 154(b) by 0 days.

(21) Appl. No.: 16/629,878

(22) PCT Filed: Jul. 12, 2017

(86) PCT No.: PCT/CN2017/092622
§ 371 (c)(1),
(2) Date: Jan. 9, 2020

(87) PCT Pub. No.: WO2019/010647
PCT Pub. Date: Jan. 17, 2019

(65) Prior Publication Data
US 2021/0147897 A1    May 20, 2021

(51) Int. Cl.
*C12Q 1/18* (2006.01)
*C12Q 1/22* (2006.01)
*C12Q 1/48* (2006.01)
*C12Q 1/66* (2006.01)

(52) U.S. Cl.
CPC .............. *C12Q 1/18* (2013.01); *C12Q 1/485* (2013.01); *C12Q 1/66* (2013.01); *C12Y 207/0104* (2013.01); *C12Y 207/04003* (2013.01)

(58) Field of Classification Search
CPC ............. C12Q 1/18; C12Q 1/485; C12Q 1/66
See application file for complete search history.

(56) References Cited

U.S. PATENT DOCUMENTS

| 3,933,592 | A | * | 1/1976 | Clendenning | ............ | C12Q 1/18 435/8 |
|---|---|---|---|---|---|---|
| 6,703,211 | B1 | | 3/2004 | Shultz et al. | | |
| 2008/0014607 | A1 | | 1/2008 | Champiat | | |
| 2012/0231961 | A1 | | 9/2012 | La Duc et al. | | |
| 2015/0305344 | A1 | * | 10/2015 | Burke | .................... | A61L 2/204 424/616 |

FOREIGN PATENT DOCUMENTS

| WO | 2004/027020 A2 | 4/2004 |
|---|---|---|
| WO | 2005/033329 A2 | 4/2005 |
| WO | 2005/093085 A1 | 10/2005 |
| WO | 2013/177229 A1 | 11/2013 |

OTHER PUBLICATIONS

Abehlo, M., "Extraction and Quantification of ATP as a Measure of Microbial Biomass: Chapter 30", Methods to Study Litter Decomposition: A Practical Guide, Springer, 223-230 (2005).
Fujinami, Y. et al., "Sensitive Detection of Bacteria and Spores Using a Portable Bioluminescence ATP Measurement Assay System Distinguishing from White Powder Materials", Journal of Health Science, 50(2): 126-132 (Jan. 2004).
Chollet, R. et al., "Use of ATP Bioluminescence for Rapid Detection and Enumeration of Contaminants: The Milliflex Rapid Microbiology Detection and Enumeration System", Bioluminescence—Recent Advances in Oceanic Measurements and Laboratory Applications, 99-118 (Feb. 2012).
Halvorson, H. et al., "Dormancy of Bacerial Endospores: Regulatio of Electron Transport by Dipicolinic Acid", Proc. N. A.S., 1171-1180 (1958).
Leggett, M.J. et al., "Bacterial spore structures and their protective role in biocide resistance", Journal of Applied Microbiology, 113: 485-498 (2012).
Lundin, A. et al., "Comparison of Methods for Extraction of Bacterial Adenine Nucleotides Determined by Firefly Assay", Applied Microbiology, 30(5): 713-721 (1975).
Omidbakhsh, N. et al., "How Reliable are ATP Bioluminescence Meters in Assessing Decontamination of Environmental Surfaces in Healthcare Settings", PLOS One, 9(6): 1-8 (Jun. 2014).
Russell, A.D., "Bacterial Spores and Chemical Sporicidal Agents", Clinical Microbiology Reviews, 99-119 (Apr. 1990).
Setlow, P. et al., "Biochemical Studies of Bacterial Sporulation and Germination", The Journal of Biological Chemistry, 245(14): 3637-3644 (Jul. 1970).
Walsh, S. et al., "An assessment of the metabolic activity of starved and vegetative bacteria using two redox dyes", Journal of Microbiological Methods, 24: 1-9 (Jan. 1995).
International Search Report and Written Opinion of the International Searching Authority for International Patent Application No. PCT/CN2017/092622 dated Apr. 18, 2018, 11 pages.
Setlow, P. et al., "Biochemical Studies of Bacterial Sporulation and Germination", The Journal of Biological Chemistry, 245(14): 3645-3652 (Jul. 1970).
Brookes et al., "The Adenylate Energy Charge of the Soil Microbial Biomass," Soil Biol. Biochem., vol. 15, No. 1, pp. 9-16 (1983).
Extended European Search Report for Application No. 17917607.8 dated Dec. 3, 2020.

* cited by examiner

*Primary Examiner* — Maryam Monshipouri
(74) *Attorney, Agent, or Firm* — Merchant & Gould P.C.

(57) ABSTRACT

Provided is a method for detecting the presence of bacterial spores by measuring adenosine diphosphate (ATP) production over time. Spores are detected by converting adenosine monophosphate (AMP) and adenosine diphosphate (ADP) to ATP.

17 Claims, No Drawings

RAPID APPROACH FOR DETECTION OF BACTERIAL SPORES

CROSS REFERENCE TO RELATED APPLICATIONS

This application is a National Stage Application of PCT/CN2017/092622, filed on Jul. 12, 2017, which is incorporated in this application by reference. To the extent appropriate, a claim of priority is made to the above disclosed application.

BACKGROUND

Endospores are dormant, tough, non-reproductive structures produced by particular species of bacteria in the *Firmicute* phylum. Endospores, or spores, are produced when bacterial cells in their vegetative state are exposed to stress or lack of nutrients. Endospores have a very low metabolic rate and therefore cannot be detected by methods typically employed to rapidly detect vegetative bacterial cells. Further, spores are extremely difficult to kill because they are designed to survive harsh conditions such as UV, heat, disinfectants, desiccation, and starvation. Upon exposure to favorable conditions and nutrients, the spores germinate to produce vegetative cells.

Spore-producing bacteria are problematic because they cause illness in humans and animals, spoilage in food and beverages, and promote the perpetuation of biofilms. Spore-producing bacterial strains that are of particular concern are those in the *Bacillus* and *Clostridium* genera. Both are gram-positive, rod-shaped bacteria that include species that are harmful to humans. *B. anthracis* produces anthrax toxin and *B. cereus* causes food poisoning. *C. botulinum* causes botulism (also known as Botox), *C. difficile* causes diarrhea, *C. perfringens* causes food poisoning, and *C. tetani* causes tetanus. *Bacillus, Paenibacillus*, and *Brevibacillus* bacteria can cause problems in food packaging board products. *Bacillus cereus* is one of the most problematic bacteria because it has been identified as possessing increased resistance to germicidal chemicals used to decontaminate environmental surfaces.

*Bacillus cereus* is frequently diagnosed as a cause of gastrointestinal disorders and has been suggested to be the cause of several food-borne illness outbreaks. Due to its rapid sporulating capacity, *B. cereus* easily survives in the environment. This bacterium can contaminate food directly and indirectly. *B. cereus* can contaminate raw milk directly via feces and soil, and can survive intestinal passage in cows and the pasteurization process. Indirect contamination can come from the presence of *B. cereus* spores in liquid and food packaging. Spores present in materials that come into direct contact with food can cause migration of spores into the food, resulting in spoilage.

Given the negative implications of these bacteria being ingested by humans, government agencies have set standards or guidelines intended to reduce the presence of spores. Current spore detection methods require 48 hours to complete. The most common way to test for bacterial spores is a plating technique. This two-day delay is impractical for many industries. In the case of product testing, a two-day delay requires an extraordinary amount of product to be quarantined until the testing results are complete. This is a problem, for example, in the paper or paperboard industry.

Likewise, when testing food and beverage processing equipment, the equipment is only taken down for cleaning periodically and, as a practical matter, cannot remain offline for two days. Hospitals cannot keep hospital rooms empty for two days while waiting for test results designed to identify the presence of spores on surfaces in a hospital room after a patient that has been infected with *C. diff.* has been discharged. And it is not practical to hold quantities of food or water under quarantine, especially where the food may spoil while waiting or where the water or fluid continually changes (e.g., cooling tower water, beverages, milk during milk processing).

Spore forming bacteria can have a negative impact on liquid packaging board product quality and machine production. Inadequate diagnosis of spore contamination of liquid packaging board product during production can result in economic losses.

It is against this background that the present disclosure is made.

SUMMARY

In general terms, this disclosure is directed to methods of rapidly detecting and distinguishing bacterial spores from vegetative cells.

In one aspect, a method of detecting and differentiating bacterial spores from vegetative cells and other microorganisms in a sample is described. The method begins by preparing a sample to be tested for the presence of bacterial spores. The sample is enriched and an initial quantity of ATP is measured. Adenosine monophosphate (AMP) and adenosine diphosphate (ADP) are extracted from the sample and enzymes convert the AMP and ADP to ATP. A final quantity of ATP is measured, wherein an increase in ATP concentration from the initial ATP measurement to the converted ATP measurement indicates the presence of spores in the sample.

In some aspects, the method of detecting and differentiating bacterial spores from vegetative cells and other microorganisms in a sample begins by preparing a sample to be tested for the presence of bacterial spores. The sample is enriched and an initial quantity of ATP is measured. AMP and ADP are extracted from the sample and enzymes convert the AMP and ADP to ATP. A final quantity of ATP is measured, wherein an increase in ATP concentration from the initial ATP measurement to the converted ATP measurement indicates the presence of spores in the sample. The method can include additional steps. In some embodiments, the sample is prepared by collecting a sample containing an unknown quantity of spores, vegetative cells or both spores and vegetative cells. The sample is disintegrated if it is solid. The sample can be collected from a hard surface, a liquid, or a paper product. The hard surface may be food and beverage processing equipment, pipes, tanks, evaporators, spray nozzles, dairy processing equipment, milk tanks, milk trucks, milking equipment, countertops, cooking surfaces, bathroom surfaces such as sinks and toilet handles, light switch panels, doorknobs, call buttons, phone handles, remote controls, desktops, patient rails, grab bars, surgical instruments, equipment inside paper mills including pipes, chests, headboxes, broke towers, saveall blades, and forming wire. The liquid may be process waters, incoming water, cooling tower water, treated and untreated wastewater, paper furnish (thin and thick stock), white water, uhle box water, tray water, fruit and vegetable flume water, protein process water, hydroponic waters or seafood farming water, and water for agricultural uses. And the paper product may be finished paper products and finished board products both for food contact and non-food contact grades; drapes for surgical or medical use; aseptic packaging containers; plastic food and beverage containers; food cans; aluminum or PET beverage containers; bags or films or modified atmosphere packaging. The spores are isolated from the sample by heating the sample at 80° C. for about 5-60 minutes, about 10-30 minutes, or about 15-20 minutes; or alternatively, the samples are heated at 100° C. for about 5-30 minutes, about 10-30 minutes, or about 15-20 minutes. The AMP and ADP are extracted from the sample with a solvent, acid, heat (e.g., 65° C. or higher for 1-10 minutes), detergent, or surfactant. The AMP and ADP are converted to ATP by treating the sample with pyruvate kinase and phosphoenolpyruvate to convert ADP to ATP, treating the sample with myokinase to convert ATP and AMP to ADP, and treating the sample with pyruvate kinase and phosphoenolpyruvate to convert ADP to ATP. The adenine nucleotide is converted to ATP with pyruvate kinase, myokinase, and phosphoenolpyruvate within about 10 minutes to 24 hours. The ATP levels in the sample are measured by either adding luciferase and luciferin to the sample and measuring light emissions in relative light units (RLUs) or by HPLC. An antimicrobial treatment will be selected and applied based upon the presence or absence of spores, vegetative cells, or both spores and vegetative cells. If spores are present, the antimicrobial treatment is selected from the group consisting of chlorine dioxide, ozone, glutaraldehyde, sodium hypochlorite, peracid, UV, extreme heat, and radiation. When only vegetative cells are present, the antimicrobial treatment is selected from the group consisting of: isothiazolin; glutaraldehyde; dibromonitrilopropionamide; carbamate; quaternary ammonium compounds; sodium hypochlorite; chlorine dioxide; peracetic acid; ozone; chloramines; bromo-sulfamate; bromo-chloro-dimethyl hydantoin; dichloro-dimethyl hydantoin; monochloramine; sodium hypochlorite used in combination with ammonium salts and stabilizers including dimethyl hydantoin amino acids, cyanuric acid, succinimide, urea; and a combination thereof. In some embodiments, the method further includes applying the selected antimicrobial treatment to the hard surface, liquid, or paper product. The method can detect spores within 2-8 hours of the sample collection.

In some aspects, the method further includes selecting an antimicrobial treatment based upon the presence or absence of spores, vegetative cells, or both spores and vegetative cells.

In some embodiments, the spores are isolated from the sample by heating the sample at about 80° C. for about 5 to 60 minutes or at about 100° C. for about 5 to 30 minutes. In some embodiments, enriching the sample involves increasing the concentration of microorganisms in the sample by centrifugation, glass bead, magic bead, or filtration.

In some aspects, AMP and ADP are extracted from the sample with solvent, acid, heat, detergent, or surfactant. In embodiments, where the samples are treated with heat, temperatures of 65° C. or higher are applied for 1 to 10 minutes.

In some embodiments, the AMP and ADP are converted to ATP by treating the sample with pyruvate kinase and phosphoenolpyruvate to convert ADP to ATP, treating the sample with myokinase to convert ATP and AMP to ADP, and treating the sample with pyruvate kinase and phosphoenolpyruvate to convert ADP to ATP. In some aspects, the adenine nucleotide is converted to ATP with pyruvate kinase, myokinase, and phosphoenolpyruvate within about 10 minutes to 24 hours.

In some aspects, measuring ATP levels in the sample is done by adding luciferase and luciferin to the sample and measuring light emissions in relative light units (RLUs). In other aspects, the ATP levels are measured by HPLC.

In some aspects, the method further includes selecting an antimicrobial treatment based upon the presence or absence of spores, vegetative cells, or both spores and vegetative cells. In some embodiments, the antimicrobial treatment is selected from the group consisting of chlorine dioxide, ozone, glutaraldehyde, sodium hypochlorite, peracid, UV, extreme heat, radiation when spores are detected. In other embodiments, the antimicrobial treatment is selected from the group consisting of: isothiazolin; glutaraldehyde; dibromonitrilopropionamide; carbamate; quaternary ammonium compounds; sodium hypochlorite; chlorine dioxide; peracetic acid; ozone; chloramines; bromo-sulfamate; bromo-chloro-dimethyl hydantoin; dichloro-dimethyl hydantoin; monochloramine; sodium hypochlorite used in combination with ammonium salts and stabilizers including dimethyl hydantoin amino acids, cyanuric acid, succinimide, urea; and a combination thereof when only vegetative cells are detected. In some embodiments, the method further includes applying the selected antimicrobial treatment to the hard surface, liquid, or paper product.

In some aspects, the method can determine a concentration of spores in a sample within 2 to 8 hours of sample collection.

DETAILED DESCRIPTION

The present disclosure is directed to methods of detecting bacterial spores. In particular, embodiments are directed to a method of rapidly distinguishing the presence of bacterial spores from the presence of other microorganisms and determining the source of a spore contamination. Furthermore, the present disclosure distinguishes between vegetative and spore states of spore-forming bacteria.

The following definitions are provided to determine how terms used in this application, and in particular how the claims, are to be construed. The organization of the definitions is for convenience only and is not intended to limit any of the definitions to any particular category.

The term "bacterial spores" or "endospores" as used herein, refers to structures produced by some species of bacteria, such as *bacillus* and *clostridium* species. Spores enable bacteria to remain dormant in harsh conditions such as extreme temperatures, drought, and chemical treatments.

The term "end-use spoilage events," as used herein, refers to times when microorganisms have grown enough to spoil a product.

The term "germination," as used herein, refers to the growth of vegetative cells from dormant bacterial spores. Germination takes place when spores are exposed to favorable conditions for vegetative cells to grow.

The term "vegetative bacterial cells," as used herein, refers to bacterial cells that are actively growing and dividing.

The term "biocide" as used herein, refers to a chemical substance or microorganism intended to destroy or neutralize any harmful organism by chemical or biological means. Biocides may include preservatives, insecticides, disinfectants, and pesticides that are used to control organisms that are harmful to human or animal health or cause damage to natural or manufactured products. Biocides are antimicrobial agents or chemical compositions that can prevent microbiological contamination or deterioration caused by microorganisms.

The term "sporicide" as used herein, refers to any substance used to kill or neutralize bacterial spores. As used in this disclosure, the term "sporicide" refers to a physical or chemical agent or process having the ability to cause greater than a 90% reduction (1-log order reduction) in the population of spores of Bacillus cereus or Bacillus subtilis within 10 seconds at 60° C. Preferably, the sporicidal compositions of the disclosure provide greater than a 99% reduction (2-log order reduction), more preferably greater than a 99.99% reduction (4-log order reduction), and most preferably greater than a 99.999% reduction (5-log order reduction) in such population within 10 seconds at 60° C.

The term "quarantine" refers to separation and isolation of organisms or objects contaminated or infected with a pathogen.

The term "rapid detection" as used herein, refers to methods of detecting bacteria and bacterial spores in less than 48 hours. Preferably, "rapid detection" refers to detecting bacteria in less than 12 hours. Most preferably, "rapid detection" refers to detecting bacteria in less than 4 hours.

The term "process water" as used herein, is water used in connection with technical plants and production processes. Process water is not consider drinkable and is used to facilitate manufacturing processes.

The term "adenosine triphosphate" (ATP) refers to a molecule used to transport chemical energy within cells. ATP contains adenine, ribose, and three phosphate groups. ATP breaks down into adenosine diphosphate (ADP) and phosphate to release energy.

The term "microorganisms" as used herein, refers to microscopic organisms that are single-celled or multicellular. These organisms may include bacteria, viruses, fungi, and algae.

The term "bioluminescence" as used herein, refers to the production and emission of light by a living organism. The enzyme luciferase catalyzes the oxidation of luciferin, producing light.

The term "high performance liquid chromatography" (HPLC) as used herein, refers to an analytical chemical technique used to separate, identify, and quantify each component in a mixture.

The term "cation" as used herein, refers to a positively charged ion.

The term "dormant" as used herein, refers to an organism having normal physical functions suspended for a period of time.

The term "colony-forming units" (CFUs) as used herein, refers to an estimate of a number of viable bacterial or fungal cells in a sample. Viable cells are able to multiply under controlled conditions CFUs are provided as a measure of CFU/mL for liquids or CFU/g for solids.

The term "relative light units" (RLUs) as used herein, refers to an amount of light as measured by a luminometer.

The term "germination conditions" as used herein, refers to conditions favorable for activation, germination, and outgrowth of bacterial spores (endospores).

Detecting the presence of bacteria and bacterial spores is important in many industries. When human health is involved, guidelines dictate the maximum amount of bacteria that may be present. For example, the "Dairymen's Standard" provides requirements for the number of colony-forming units (CFU) of bacteria that may be present per gram of paper or paperboard to be used in dairy products. Samples are cut from the paper or paperboard to be tested and are placed in sealed envelopes. The sample is then cut into small squares and deposited in a sterile blender. Sterile phosphate dilution water is added to the cut up paper sample in the blender to help disintegrate the sample. Immediately after disintegration, the sample is transferred into one or more petri dishes. Melted agar is poured over the sample in the petri dish and allowed to solidify. Upon solidification, the plates are incubated at 36° C. for 48 hours. After incubation, the plates are examined for the presence and number of CFU with a colony counter.

Industry guidelines limit the number of colony forming units (CFU) present on paper or paperboard products used with dairy products to less than 250 per gram. Some end users may require more or less stringent compliance (<100→1000 CFU/g). In order to comply with spore guidelines for the dairy, food, and healthcare industries, it is important that bacteria that can form spores are detected and properly treated when they are in their most vulnerable, vegetative, state.

Spores are made up of many protective layers that make them resistant to oxidation and chemical attack. Higher biocide doses are needed to kill spores than vegetative cells. It is always more effective to apply biocide to active, vegetative cells. A spore control program must be robust enough to attack cells in the vegetative state and prevent sporulation. Dosages must be high enough to kill vegetative cells before they develop into spores.

Adenosine triphosphate (ATP) measurements have been used for detecting microorganisms in various industries. ATP is used by cells as a source of energy and is an indicator of metabolic activity. ATP can be measured in vegetative bacteria, but bacterial spores contain little to no ATP.

ATP levels are typically measured by a bioluminescence assay involving reactions with luciferase that are quantified with a luminometer. Other methods include colorimetric or fluorometric assays utilizing phosphorylation of glycerol and high performance liquid chromatography (HPLC).

In the method utilizing bioluminescence, luciferase and luciferin from fireflies are mixed with a sample with a cation, such as magnesium, in the presence of oxygen. If ATP is present, it will cause a reaction between luciferase (the substrate) and luciferin (the catalyst) in an oxidation reaction which produces light. Light emissions are detected with a luminometer and reported in relative light units (RLUs). The amount of light produced is proportional to the metabolic activity of microbial organisms present, but does not indicate the amount of organisms present. The luciferase/luciferin reaction is well known in the art, and there are commercial sources for the necessary reagents as well as protocols for their use. For example, several luciferase/luciferin reagents along with luciferase are available in commercial kits from, for example, Promega Corp. (Madison, Wis.) and Luminultra (Fredericton, New Brunswick). Commercially available luciferases include firefly luciferase (Photinus pyralis, "Ppy luciferase"). Purified beetle luciferin is also commercially available from Promega.

As was mentioned above, while vegetative bacterial cells produce a lot of ATP, spores produce very little ATP. About 80% of adenine nucleotide (AN) in vegetative cells is ATP, while in spores that Figure is 1% or less. However, spores contain a lot of adenine nucleotide (AN) as AMP and ADP. AMP and ADP cannot be detected with luminescent techniques, but AMP and ADP can be extracted from bacterial spores. Addition of certain enzymes converts AMP and ADP into ATP. The ATP can then be quantified with luminescent techniques. These ATP measurements can be used to estimate a spore count within a sample. Surprisingly, this method can quantify the number of spores present in a sample in as little as one hour.

To implement this method for the rapid detection of bacterial spores in an industrial process, a sample must first be prepared which will be tested for the presence of bacterial spores. The sample may be collected from any source which could be contaminated with bacterial spores. The sample may be contaminated with bacterial spores, with vegetative bacterial cells, neither, or both. The sample may be taken from a hard surface, a slurry, stock fibers, a food or beverage product, a liquid, or packaging or a paper board product sample.

Non-limiting examples of facilities having hard surfaces include food and beverage plants, dairy plants, farms and dairies, breweries, ethanol plants, full service and quick service restaurants, grocery stores, warehouse and retail stores, commercial or office space, hotels, motels, hospitals, paper mills, industrial manufacturing plants including automotive plants, cooling towers, water treatment plants, refineries, oil and gas fields and pipelines, and drilling platforms. Examples of hard surfaces include food and beverage processing equipment including pipes, tanks, evaporators, spray nozzles and the like, dairy processing equipment, milk tanks, milk trucks, milking equipment, countertops, cooking surfaces, bathroom surfaces such as sinks and toilet handles, light switch panels, doorknobs, call buttons, phone handles, remote controls, desktops, patient rails, grab bars, surgical instruments, equipment inside paper mills including pipes, chests, headboxes, broke towers, saveall blades, forming wire, and the like.

Samples on hard surfaces may be taken with a sterile swab or other sterile device that can be used to collect microorganisms from a hard surface, such as: medical tape, cotton cloth, cellulose cloth, and the like. If the surface is dry, a solvent may be applied with a swab to dissolve any bacterial residue that may be present and suspend the residue in the solvent for testing. Examples of solvents can include, but are not limited to: sterile water, sterile phosphate buffer, sterile Tris EDTA (TE) buffer, a dilute detergent solution such as TWEEN, and the like.

Non-limiting examples of liquids include process waters, incoming water, cooling tower water, treated and untreated wastewater, paper furnish (thin and thick stock), white water, uhle box water, tray water, fruit and vegetable flume water, protein (e.g., poultry, pork, red meat, seafood) process water, hydroponic waters or seafood farming water, water for agricultural uses. Samples of liquids may be aliquoted into sterile containers from the source of potential contamination.

Non-limiting examples of food and beverage products include milk, beer, wine, drinking water, fruits and vegetables, protein such as poultry, pork, red meat or seafood, ready-to-eat meat, cheese, prepared foods, frozen foods, ice cream.

Non-limiting examples of packaging and products include: paper products such as finished paper products and finished board products both for food contact and non-food contact grades; drapes for surgical or medical use; aseptic packaging containers; plastic food and beverage containers (e.g., yogurt containers, milk containers, deli containers); food cans (e.g., soup cans); aluminum or PET beverage containers; bags or films or modified atmosphere packaging. The products can be tested before they leave the manufacturing facility, for example, at the paper mill, or at the point of use such as at the food or beverage plant. Samples of paper products may be tested according to the procedure described in the Dairyman's Standard (TAPPI Test Method T449 Bacteriological Examination of Paper and Paperboard, or ISO8784 Pulp and Board Microbiological Examination).

Initial ATP level of the samples are measured and recorded as "ATPoriginal." ATP measurements are taken by a luminescent approach. As described above, the sample may be combined with luciferase and luciferin along with a cation, oxygen and tris buffer or similar buffer. Light produced by the reaction is measured in relative light units (RLUs). The measurement may be taken with a luminometer. Alternatively, the ATP measurement may be taken by HPLC.

The samples are heated to destroy vegetative cells. In some embodiments, samples are heated at 80° C. for about 5 to 60 minutes, preferably about 10 to 30 minutes, and more preferably about 15 to 20 minutes. In other embodiments, the samples are heated at 100° C. for about 5 to 30 minutes, preferably about 10 to 30 minutes, and more preferably about 15 to 20 minutes. ATP level is measured as surviving spore forming bacteria and record as "ATPheat."

Spores are enriched in the sample by one or more of centrifugation, glass bead, magic bead, and filtration techniques. In some embodiments, the spores are extracted by subjecting the spore sample to temperatures of about 60° to 65° C. for about 1 to 30 minutes, preferably 1 to 20 minutes, and most preferably 5 to 15 minutes.

The enriched sample is then treated with solvent, acid, or heat, including but not limited to n-propyl alcohol, nitrite salt, trichloroacetic acid, ultrasonic, detergent, protein degrading agent, denaturing agent, surfactant, and divalent metal.

The extracted sample is then treated with Pyruvate kinase (PK), Myokinase (MK), and phosphoenolpyruvate (PEP) to convert ADP and AMP to ATP. This conversion takes place within 10 minutes to 24 hours. Preferably, the conversion occurs within 15 minutes to 2 hours. Most preferably, the conversion occurs within 15 minutes. The following chemical equations summarize the conversion process:

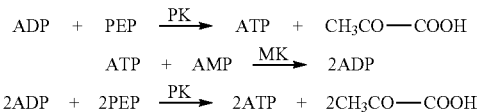

Another ATP measurement is taken of the sample after conversion is complete. The ATP level of spore-forming bacteria is recorded as "ATPconversion."

The significant difference between the measurements for "ATPoriginal" and "ATPheat" indicate that the vegetative cells are destroyed. The level of "ATPconversion" is normally increased compared to "ATPheat." The magnitude of ATP level increase indicates the presence of spore forming bacteria. If there is only vegetative cells, the "ATPconversion" measurement will not be significantly increased by comparison to the "ATPheat" measurement.

Once it has been determined that spores are present in the sample, an antimicrobial treatment is selected. If spores are detected, treatments may be selected from the following: oxidizing biocide chlorine dioxide, ozone, glutaraldehyde, sodium hypochlorite, monochloramine, peracids and mixture thereof; non-oxidizing-biocide include but not limited to alcohols, isothiazolin, dibromonitrilopropionamide (DBNPA), quaternary ammonium compounds, bronopol (BNPD), bis-trichloromethyl sulfone, methylene bis thiocyanate, 1-(3-chloroallyl)-3,5,7-triaza-1-azoniaadamantane, tetrakis(hydroxymethyl) phosphonium sulphate (THPS), (thiazolyl)bendimidazole and combinations thereof. To achieve sporicidal efficacy, the concentration of the biocide should be higher than the treatment dosage used as biocidal; normally from 0.1 ppm to 5000 ppm in the liquid, or 0.001% to 0.5% for surface, solid or slurry treatment.

Non-chemical treatments like extreme heat and UV radiation can also be used. Targeting spore-forming bacteria when they are in their vegetative state expands the list of effective biocides to include DBNPA, isothiazolin, quaternary amines, and the like. Once an appropriate treatment has been selected, it is applied to the part of the process where spore-forming bacteria are present in a vegetative state when no spores are detected. This could include a hard surface, food or beverage product, liquid, package, or paper product at the point in production where the contamination has been detected.

Because the method takes no longer than 8 hours to complete, the bacterial contamination can be eliminated quickly to prevent spore formation downstream. Additionally, the treatment can be done while equipment is offline for cleaning or without quarantining product for multiple shifts and production problems can be corrected more quickly. After the application of treatment, a subsequent round of testing should take place to ensure elimination of spores has taken place. The ability to act with the correct chemical in the correct place in production results in both cost and time savings.

For a more complete understanding of the present disclosure, the following examples are given to illustrate some embodiment. These examples and experiments are to be understood as illustrative and not limiting. All parts are by weight, except where it is contrarily indicated.

EXAMPLES

Example 1: Conversion of AMP and ADP to ATP to Detect Bacterial Spores

Bacillus subtilis was used as the testing spore forming bacterial strain. B subtilis cultures were grown on plates with TSB agar at 36±2° C. for 24 h. The plates were scraped and the cultures are suspended in sterile water, transferred to a bottle flat, and incubated at 32±2° C. for 24 h. The sample was then centrifuged for 5 minutes at 5000 rpm. The excess fluid above the pellet was removed, the pellet was washed with sterile phosphate buffer, and centrifuged again. The pellet was re-suspended in phosphate buffer to a 50 mL volume and recorded as "original". The spore suspension were prepared by immersing the harvested sample in a water bath for 15 minutes at 80° C. and recorded as "spore suspension". Before treatment with extraction agent, the sample was treated at 60° C. for 10 minutes. The prepared spore sample was divided into two parts. The first part was undiluted and the second one was diluted 10 times. Total aerobic bacteria count (TABC) and ATP were measured and listed in Table 1.

TABLE 1

ATP and TABC level of prepared endospore before conversion

| | Treatment | | | |
|---|---|---|---|---|
| | 5000 rpm, 5 min | 80° C., 15 min(Spore suspension) | 60° C., 10 min(Spore) | |
| | "ATPoriginal" | "ATPheat" | 1st | 2nd |
| ATP, RLU | 853358 | 1298 | 1053 | 45 |
| TABC, cfu/ml | $1 \times 10^8$ | $1.6 \times 10^5$ | $2.5 \times 10^5$ | $2 \times 10^4$ |

$2^{nd}$ sample diluted 10 times of 1st sample.

The spore samples were then extracted by different methods including N-propanol, centrifugation, and ultrasonic. ATP was measured and listed in Table 2. ATP levels did not increase after extraction procedure.

TABLE 2

ATP level of samples treated with different extraction approaches

| | | Treatment | | | |
|---|---|---|---|---|---|
| | | No treatment | N-propanol 5 mins | Centrifuge + N-propanol | Ultrasonic 10 min |
| 1st | ATP, RLU | 311 | 54 | 199 | 301 |
| 2nd | ATP, RLU | 45 | 6 | 59 | 23 |

After extraction, the samples were treated with pyruvate kinase (PK), Myokinase (MK) and Phosphoenolpyruvate (PEP) to convert ADP and AMP to ATP. ATP was measured by Luminescent method. The ATP level was measured and listed in Table 3. ATP levels increased significantly after conversion in the sample which was extracted with centrifugation and N-propanol.

TABLE 3

ATP level after conversion

| | No Treatment | N-propanol with water | Centrifuge + N-propanol | Ultrasonic 10 min |
|---|---|---|---|---|
| $1^{st}$ ATP, RLU | 302 | 144 | 28194 | 220 |
| $2^{nd}$ ATP, RLU | 75 | 117 | 9918 | 48 |

When spore suspension was prepared, the ATP reading in the sample was measured at 1298 RLU, while the spore count was $1.6 \times 10^5$ cfu/ml. So the ATP reading does not correlate with the existence of spore-forming bacteria. The results indicated that after extraction with N-propanol and conversion of AN to ATP, the ATP reading was increased significantly. The ATP reading of 28194 and 9918 RLU was corresponding to spore plate count $2.5 \times 10^5$ cfu/mL and $2 \times 10^4$ cfu/ml respectively.

Example 2: Spore Detection with ATP Conversion Method

Bacillus subtilis Spore suspension was prepared as described in example 1, except that after incubation at 32±2° C. for 24 h, the culture was put into refrigerator for 9 days then heated at 80° C. for 20 min to prepare a spore suspension which was generated for a longer time. Before the extraction procedure, the spore suspension was not treated at 60° C. as described in example 1.

TABLE 4

ATP and TABC of Prepared Endospore

| | 8000 rpm, 5 min "Spore forming bacteria" | 80° C., 20 min "Spore suspension" |
|---|---|---|
| ATP, RLU | 20199 | 239 |
| TABC, cfu/ml | $1 \times 10^7$ | $1.04 \times 10^5$ |

The Spore suspension was then extracted and converted by enzyme. The results of TABC and ATP level are listed in Tables 5. Extraction by TCA and N-propanol increased ATP level significantly compared to no extraction treatment process.

TABLE 5

After conversion, the test results of ATP in the samples

| | 20 mM MgSO4, heat 100° C. "ATPconversion" | 2.5% TCA "ATPconversion" | Centrifuge + N-propanol "ATPconversion" | No treatment "ATPconversion" |
|---|---|---|---|---|
| ATP, RLU | 22 | 2342 | 5129 | 105 |

A different loading of spore suspension was prepared as described in example 2, after extraction and conversion, ATP level was increased to 17894 RLU compared to 655RLU in spore suspension without treatment.

TABLE 6

After conversion, the test results of ATP in the samples

| | 5000 rpm, 5 min "ATPoriginal" | 80° C., 40 min (Spore Suspension) "ATPheat" | N-propanol "ATPconversion" |
|---|---|---|---|
| ATP, RLU | $9.17 \times 10^5$ | 655 | 17894 |
| TABC, cfu/ml | $1.5 \times 10^9$ | $6 \times 10^6$ | $6 \times 10^6$ |

In summary, the present method can rapidly identify spore-forming bacteria by making low levels of ATP readable in dominant spores to a significant level that can correlate to plate count through enrichment, extraction and conversion processes.

What is claimed is:

1. A method of reducing bacterial spores or vegetative cells comprising:
    preparing a sample to be tested for the presence of bacterial spores and vegetative cells, the sample taken from a hard surface, a liquid, or a paper product;
    measuring an initial quantity of adenosine triphosphate (ATP) ($ATP_{original}$);
    heating the sample to destroy any vegetative cells;
    measuring the quantity of ATP after heating the sample ($ATP_{heat}$);
    concentrating bacterial spores or vegetative cells in the sample;
    extracting adenosine monophosphate (AMP) and adenosine diphosphate (ADP) from the sample;
    converting AMP and ADP to ATP;
    measuring a final quantity of ATP ($ATP_{conversion}$),
    wherein the presence of ATP in the $ATP_{original}$ measurement indicates the presence of vegetative cells, a decrease in the ATP from $ATP_{original}$ measurement to $ATP_{heat}$ measurement indicates that the vegetative cells were destroyed by heating, and an increase in ATP concentration from $ATP_{heat}$ measurement to $ATP_{conversion}$ measurement indicates presence of bacterial spores;
    selecting an antimicrobial treatment based upon the presence or absence of bacterial spores, vegetative cells, or both bacterial spores and vegetative cells; and
    applying the antimicrobial treatment to the hard surface, the liquid, or the paper product to reduce the bacterial spores, vegetative cells, or both bacterial spores and vegetative cells.

2. The method of claim 1, the heating comprising heating the sample at about 80° C. for about 5 to 60 minutes or at about 100° C. for about 5 to 30 minutes.

3. The method according to claim 1, wherein the preparing comprises:
    collecting a sample containing an unknown quantity of bacterial spores, vegetative cells, or both bacterial spores and vegetative cells; and
    disintegrating the sample, if solid.

4. The method of claim 1, wherein the hard surface is selected from the group consisting of: food and beverage processing equipment, pipes, tanks, evaporators, spray nozzles, dairy processing equipment, milk tanks, milk trucks, milking equipment, countertops, cooking surfaces, bathroom surfaces, sinks, toilet handles, light switch panels, doorknobs, call buttons, phone handles, remote controls, desktops, patient rails, grab bars, surgical instruments, equipment inside paper mills including pipes, chests, headboxes, broke towers, saveall blades, and forming wire.

5. The method of claim 1, wherein the liquid is selected from the group consisting of: process waters, incoming water, cooling tower water, treated and untreated wastewater, paper furnish (thin and thick stock), white water, uhle box water, tray water, fruit and vegetable flume water, protein process water, hydroponic waters or seafood farming water, and water for agricultural uses.

6. The method of claim 1, wherein the paper product is selected from the group consisting of: paper products, finished paper products, finished board products, food contact grade finished board, non-food contact grade finished board, drapes for surgical or medical use, and aseptic packaging containers.

7. The method according to claim 1, wherein the concentrating comprises increasing the concentration of vegetative cells and bacterial spores in the sample by centrifugation, glass bead, magic bead, or filtration.

8. The method according to claim 1, wherein the extracting comprises treating the sample with solvent, acid, or heat.

9. The method according to claim 8, wherein the extracting further comprises treating the sample with detergent or surfactant.

10. The method according to claim 1, wherein the bacterial spores are extracted using temperatures of 65° or higher for 1 to 10 minutes.

11. The method according to claim 1, wherein the converting comprises:
    treating the sample with pyruvate kinase and phosphoenolpyruvate to convert ADP to ATP;
    treating the sample with myokinase to convert ATP and AMP to ADP; and
    treating the sample with pyruvate kinase and phosphoenolpyruvate to convert ADP to ATP.

12. The method of claim 1, wherein the AMP and ADP are converted to ATP with pyruvate kinase, myokinase, and phosphoenolpyruvate within about 10 minutes to 24 hours.

13. The method according to claim 1, wherein the measuring comprises:
    adding luciferase and luciferin to the sample; and
    measuring light emissions in relative light units (RLUs).

14. The method according to claim 1, wherein the measuring comprises measuring ATP levels by HPLC.

15. The method of claim 1, wherein the antimicrobial treatment is selected from the group consisting of chlorine dioxide, ozone, glutaraldehyde, sodium hypochlorite, peracid, UV, extreme heat, radiation when bacterial spores are detected.

16. The method of claim 1, wherein the antimicrobial treatment is selected from the group consisting of: isothiazolin; glutaraldehyde; dibromonitrilopropionamide;

carbamate; quaternary ammonium compounds; sodium hypochlorite; chlorine dioxide; peracetic acid; ozone; chloramines; bromo-sulfamate; bromo-chloro-dimethyl hydantoin; dichloro-dimethyl hydantoin; monochloramine; and a combination thereof when only vegetative cells are detected.

17. The method according to claim 1, wherein a concentration of bacterial spores in the sample can be determined within 2 to 8 hours of sample collection.

\* \* \* \* \*